US006998257B2

(12) United States Patent
Vreeland

(10) Patent No.: US 6,998,257 B2
(45) Date of Patent: Feb. 14, 2006

(54) RECOMBINANT MINIMAL CATALYTIC VANADIUM HALOPEROXIDASES AND THEIR USES

(75) Inventor: Valerie Vreeland, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 31 days.

(21) Appl. No.: 10/691,383

(22) Filed: Oct. 21, 2003

(65) Prior Publication Data

US 2004/0110260 A1 Jun. 10, 2004

Related U.S. Application Data

(60) Division of application No. 09/596,794, filed on Jun. 19, 2000, now Pat. No. 6,656,715, which is a continuation-in-part of application No. 09/151,189, filed on Oct. 10, 1998, now Pat. No. 6,232,457.

(51) Int. Cl.
*C12N 9/02* (2006.01)
*C08G 69/26* (2006.01)
*C08G 75/14* (2006.01)
*C12P 7/00* (2006.01)

(52) U.S. Cl. .................. 435/189; 530/350; 530/387.3; 435/132

(58) Field of Classification Search ................ 435/189, 435/25, 132; 536/23.5; 530/350, 387
See application file for complete search history.

(56) References Cited

U.S. PATENT DOCUMENTS

2002/0035245 A1 3/2002 Vreeland

FOREIGN PATENT DOCUMENTS

WO WO 95/27046 3/1995

OTHER PUBLICATIONS

Vilter H., Vanadium dependent haloperoxidases, in Sigel H. Siegel A. (eds.), Metal Ions in Biological System—Vanadium and its Role in Life, Marcel Dekker, New York 1995, pp. 323-362.*
Ford C. et al., Fusion Tails for the Recovery and Purification of Recombinant Proteins, Protein Expression and Purification, 1991, vol. 2, 95-107.*
Hemrika et al.; *PNAS* (1997) No. 94, pp. 2145-2149.
Itoh et al.; *J. Biological Chemistry* (1986) No. 261, pp. 5194-5200.
Pfeifer, et al.; *J. Gen. Microbiol* (1992) No. 138, pp. 1123-1131.
Rush, et al.; *FEBS Letters* (1995) 359:244-246.
Sheffield et al.; *Phytochemistry* (1993) No. 32, pp. 21-26.
Shimonshi et al.; "Cloning and Expression of the Gene for a Vanadium-dependent Bromoperoxidase from a Marine Macro-alga, Corallina pilulifera" *FEBS Lett.* (1998) No. 428, pp. 105-110.
Simons et al.; *European Journal of Biochem* (1995) No. 229, pp. 566-574.
Soedjak, et al. "Inhibition and Inactivation of Vanadium Bromoperoxidase by the Substrate Hydrogen Peroxide and Further Mechanistic Studies" *Biochemistry* (Oct. 1995) vol. 34(39), pp. 12689-12696.
Soedjak, et al. "Mechanism of Dioxygen Formation Catalyzed by Vanadium Bromoperoxidase From Macrocystis pyrifera and Fucus distichus: Steady State Kinetic Analysis and Comparison to the Mechanism of V-BrPO from Ascophyllum nodosum" *Biochim Biophys Acta.* (Aug. 1991) vol. 1079(1), pp. 1-7.
Soedjak, et al. "Characterization of Vanadium Bromoperoxidase from Macrocystis and Fucus: Reactivity of Vanadium Bromoperoxidase Toward Acyl and Alkyl Peroxides and Bromination of Amines" *Biochemistry* (Aug. 1990) vol. 29(34), pp. 7974-7981.
van Pee, K.H.;*J. Bacterioll* (1988) No. 170, pp. 5890-5894.
Vreeland et al.; *Molecular Biology of the Cell 7* (Supplement) 304a (1996).
Whitwam, R.E.; "Biophys. Research Communications." *Biochem* (1995) No. 216, pp. 1013-1017.
Wever R. et al. V. Vanadium haloperoxidases, Vanadium in Biological Systems, Physiology and Biochemistry, Chasten N.D. ed., Kulwer Academic Press, Dordrecht 1990, pp. 81-97.
Butler A. Mechanistic considerations of the vanadium haloperoxidases, coordination chemistry Reviews, 1999, 187, 17-35.
Colpas G.J. A functional model of vanadium haloperoxidases, J. Am. Chem. Soc. 1994, 116, 3627-3628.

* cited by examiner

*Primary Examiner*—Rebecca E. Prouty
*Assistant Examiner*—Malgorzata Walicka
(74) *Attorney, Agent, or Firm*—Townsend and Townsend and Crew LLP

(57) ABSTRACT

The present invention provides new recombinantly produced vanadium haloperoxidases. The enzymes are useful in a number of industrial applications.

10 Claims, 5 Drawing Sheets

Figure 3
Recombinant *Fucus* Vanadium Peroxidase Proteins

| | | # of Amino acids | kDa | VPx activity |
|---|---|---|---|---|
| rVPx1 | M1 — A676 | 676 | 73.4 | + |
| rVPx2 | A137 — A676 | 540 | 58.6 | + |
| rVPx3 | L313 — A676 | 364 | 40.0 | + |
| F1 | E343 — A676 | 334 | 36.8 | + |
| F2 | G373 — A676 | 304 | 33.4 | + |
| F3 | Y404 — A676 | 273 | 29.8 | + |
| F4 | V435 — A676 | 242 | 26.5 | + |
| R5 | L313 — F632 | 320 | 35.5 | + |
| R6 | L313 — Q652 | 340 | 37.6 | + |
| F1R6 | E343 — Q652 | 310 | 34.4 | + |
| F2R6 | G373 — Q652 | 280 | 31.0 | + |
| F4R5 | V435 — F632 | 198 | 21.7 | + |

| Amino Acid Site in rVPx1 Fucus Enzyme | Potential Amino Acid Role in vanadate-binding motifs 1-3 | Amino acid at Corresponding Ascophyllum Site |
|---|---|---|
| Lys460 | Vanadium Binding - 1st | Lys341 |
| Arg468 | Vanadium Binding - 1st | Arg349 |
| Ser535 | Vanadium Binding- 2nd | Ser416 |
| Gly536 | Vanadium Binding- 2nd | Gly417 |
| His537 | Vanadium Binding- 2nd | His418 |
| Arg599 | Vanadium Binding - 3rd | Arg480 |
| His605 | Vanadium Binding - 3rd | His486 |
| His464 | In BrPx Only - 1st | His345 |
| His530 | In BrPx Only - 2nd | His411 |
| Ala455 | Activity -1st | Ser336 |
| Cys457 | Activity - 1st | Trp338 |
| Val525 | Activity - 2nd | Glu406 |

FIG. 4

1st Conserved Motif:

| | |
|---|---|
| AQRASCYQKWQVHRFARPEALG | Fucus |
| AxxxxxYQKxxxHRxxRPEAxG | Algal |
| AxxxxxxxxKxxx(x)xxxRPxx(x)G | Algal and Fungal |
| Kxxx(x)xxxRP | Algal, Fungal, Phosphatases & Other Proteins |

(x) = amino acid present in algal enzymes only

2nd Conserved Motif:

| | |
|---|---|
| PTHPSYPSGHATQNGAFAT | Fucus |
| PxHPSYxSGHAxxxGA | Algal |
| PxxPxYxSGHAxxxGA | Algal and Fungal |
| (SY)PSGH | Algal, Fungal, Phosphatases & Other Proteins |

(SY) = conserved in some of the proteins

3rd Conserved Motif:

| | |
|---|---|
| NKLAVNVAFGRQMLGIHYRFD | Fucus |
| NKLAxNxAxGRxMxGxHYxxD | Algal |
| AxxRxxxGxHxxxD | Algal and Fungal |
| Rxx(G)xHxxx(D) | Algal, Fungal, Phosphatases & Other Proteins |

FIG. 5

RECOMBINANT MINIMAL CATALYTIC VANADIUM HALOPEROXIDASES AND THEIR USES

This application is a division of U.S. patent application Ser. No. 09/596,794, filed Jun. 19, 2000, now U.S. Pat. No. 6,656,715. This application is also a continuation in part of U.S. patent application Ser. No. 09/151,189, filed Sep. 10, 1998, now U.S. Pat. No. 6,232,457, the disclosure of which is incorporated by reference in the entirety.

FIELD OF THE INVENTION

The present invention relates to cloning and recombinant expression of proteins. In particular, it relates to expression of vanadium haloperoxidase polypeptides.

BACKGROUND OF THE INVENTION

Vanadium haloperoxidase enzymes are useful in industrial catalysis in a variety of contexts (Sheffield, et al., *Biotechnology Techniques*, 8:579–582 (1994)). For instance, they catalyze a variety of halogenation, oxidation and epoxidation reactions (Itoh, et al., *Eur. J. Biochem.*, 172:477 (1988); Itoh, et. al. *Biochimica et Biophysica Acta.*, 1994 (1993); Itoh, et al., *Appl. Microbiol. & Biotechnol.*, 43:394–401 (1995)). Although a halide ion is a required cofactor for enzyme activity, products may not be halogenated. Numerous uses in synthetic organic chemistry include reactions with diverse substrates such as aliphatic and aromatic hydrocarbons, phenols, β-diketones and nitrogen- and sulfur-containing heterocycles (Itoh, et al., *Eur. J. Biochem.* 172:477 (1988); Neidleman et al., *Biohalogenation: Principles, Basic Roles and Applications*, Ellis Horwood, John Wiley & Sons, New York (1986)). Bromoperoxidases can also be used in place of synthetic organic chemistry reactions to make activated intermediates or products such as pesticides. In addition, these enzymes have an advantage over chemical synthesis in producing stereospecific products (Itoh, et al., *Eur. J. Biochem.*, 172:477 (1988)). Moreover, haloperoxidases have unusual stability (both temporal and thermal) and are active in solvents including methanol, ethanol and acetone.

Recent medical applications of bromoperoxidase have been described. Lovqvist, et al., *Nuclear Medicine and Biology*, 22:125–131 (1995) described the enzymatic bromination of a monoclonal antibody with BR-radionuclide for imaging of antibody localization by PET scanning. There is current interest in enzymatic production of antibiotics including fosfomycin and pyrrolnitrin (Itoh, et. al. *Biochimica et Biophysica Acta.* 1994 (1993); Itoh, et al., *Appl. Microbiol. &Biotechnol.* 43:394–401 (1995)) and 7-chlorotetracycline (van Pée, K. H., *J. Bacteriol.*, 170:5890–5894 (1988)) via haloperoxidase-catalyzed reactions in bacteria.

Known haloperoxidases include bromoperoxidases from brown and red algae including *Fucus* and *Ascophyllum* (Butler, et al., *Chem. Rev.*, 93:1937–1994 (1993)), iodoperoxidase from green algae (Mehrtens, G., *Polar Biol.* 14:351–354 (1994)), and chloroperoxidase from the fungus *Curvularia inaequalis* (Van Schijndel, et al., *Eur. J. Biochem.*, 225:151–157 (1994)). A vanadate requirement for algal haloperoxidase was first described by Vilter (Vilter, H., *Biological Systems*, 31, *Vanadium and its role in life*, Sigel, et al. (Eds.), Marcel Dekker, New York, N.Y., pp. 325–362 (1995)).

The specific bromoperoxidase activity of the native *Fucus* enzyme is several fold higher (Butler, et al.) than the other algal enzymes for which at least partial sequences have been reported, *Ascophyllum* (Vilter 1995) and *Corallina* (Shimonishi, et al. FEBS Letters, 428, 105–110 (1998)), and higher specific activity than the *Curvularia* fungal chloroperoxidase (van Schijndel et al. BBA 1161:249–256 (1993)).

Extracted and partially purified bromoperoxidase from the red alga *Corallina officinalis* is commercially available from Sigma Chemical Company. Sigma has also investigated immobilization of enzyme on agarose beads (Sheffield, et al., *Phytochemistry*, 38:1103–1107 (1995)) and on cellulose acetate membrane (Sheffield, et al., *Biotechnology Techniques*, 8:579–582 (1994)) for repetitive catalysis of bromination reactions in flow-through reactors in enzyme-driven preparative organic chemistry. Many industrial uses for stable soybean peroxidase are envisioned by A. Pokora of Enzymol International, Inc. as described by Wick (Wick, C. B., *Genetic Engineering News*, 16(3):1, 18–19). Recombinant enzyme biotechnology is of current industrial interest because enzymes are safe, low-polluting alternatives to chemicals in many applications, and can be modified by protein engineering to fit the requirements of specific applications (Kelly, E. B. *Genetic Engineering News*, 16(5):1, 30, 32 (1996) Lovqvist, et al., *Nuclear Medicine and Biology*, 22:125–131 (1995)). Peroxidases can also be incorporated into moldable plastics (Service, R. F., *Science* 272:196–197 (1996)).

Multiple representatives of other classes of peroxidases have been produced in recombinant form. A heme peroxidase, manganese peroxidase from the fungus *Phanerochaete chrysosporidium*, was expressed in recombinant form and refolded for activity (Whitwam, R. E., *Biochem. Biophys. Research. Communications*, 216:1013–1017 (1995)). Recombinant horseradish peroxidase isozyme C (a heme peroxidase) for use in chemiluminescent labeling in molecular biology and biotechnology applications has been described (EP 0299682, WO 89/03424 ). Recombinant non-heme haloperoxidases have been prepared from the bacteria, *Pseudomonas pyrrocinia* (Wolfframm, et al., *Gene* 130: 131–135 (1993)) and two related *Streptomyces aureofaciens* enzymes (van Pée, K. H., *J. Bacteriol.*, 170:5890–5894 (1988); Pfeifer, et al., *J. Gen. Microbiol.* 138:1123–1131 (1992)).

The X-ray structure for the fungal chloroperoxidase from *Curvularia* has been reported Messerschmidt and Wever., *Proc. Natl. Acad. Sci. U.S.A.* 93:392–396 (1996). The chloroperoxidase consisted of two helical bundle domains organized as an N-terminal noncatalytic bundle and a C-terminal catalytic bundle. The X-ray structure of the bromoperoxidase from the brown alga *Ascophyllum* (Weyand et al *J. Mol. Biol.* 293:595–611 (1999)) and the bromoperoxidase from the red alga *Corallina* (Littlechild *Curr, Opin. Chem. Biol.* 3:28–34 (1999)) have been published.

Despite the interest in vanadium haloperoxidases, there are relatively few reports in the literature of the cloning and recombinant expression of a vanadium haloperoxidases. Shimonshi et al. *FEBS Lett.* 428:105–110 (1998) described cloning of the enzyme from *Corallina pilulifera*. Cloning of the *Curvularia* gene is described by Hemrika, et al. *PNAS* 94,2145–2149 (1997) and 95/27046. A partial sequence of the *Ascophyllum* gene is described in Vilter (1995). There is a need in the art for efficient means for producing vanadium haloperoxidases using techniques such as recombinant expression. The present invention addresses these and other needs.

SUMMARY OF THE INVENTION

The present invention provides isolated nucleic acids comprising a polynucleotide sequence encoding a vanadium haloperoxidase polypeptide consisting of a catalytic helical frame that complexes a vanadium ion and catalyzes the oxidation of o-dianisidine (ODA). The polypeptides of the invention preferably comprise amino acids unique to the *Fucus* haloperoxidase. Examples include an Ala residue at a position corresponding to position 455 of SEQ ID NO: 2, a Cys residue at a position corresponding to position 457 of SEQ ID NO: 2, or a Val residue at position 525 of SEQ ID NO: 2.

In some embodiments, the haloperoxidase polypeptide comprises an amino acid sequence having at least about 70% amino acid sequence identity to an amino acid sequence from residue 435 to residue 632 as set forth in SEQ ID NO:2. The polypeptide may have a molecular weight of about 20 kDa. The isolated nucleic acid will usually have a polynucleotide sequence at least about 70% sequence identity to a subsequence as of SEQ ID NO:1.

To facilitate recombinant expression, the polynucleotide sequence is often included in a recombinant expression cassette in which the polynucleotide sequence is operably linked to a promoter sequence. The invention also provides cells comprising the expression cassette of the invention.

In some embodiments, the polypeptides of the invention are immobilized on a solid surface. The polypeptide may further comprise a cleavable linker sequence, such as an enterokinase cleavable linker sequence. The polypeptide may also further comprise an purification tag, such as a plurality of histidine residues.

The invention also provides method for enzymatically halogenating or oxidizing a compound using the enzymes of the invention.

The invention further provides method for preparing active vanadium haloperoxidase polypeptides of the invention using preferred methods of refolding. The refolding may comprise contacting the vanadium haloperoxidase polypeptide with an ammonium sulfate solution with or without magnesium sulfate. In other embodiments, the method use magnesium sulfate, preferably at about 0° C. to about 10° C. Still further methods of refolding comprise contacting the vanadium haloperoxidase polypeptide with imidazole and sodium or potassium chloride, preferably at about 10° C. to about 17° C.

DEFINITIONS

A "vanadium haloperoxidase polypeptide" of the invention is an isolated protein capable of catalyzing the oxidation of o-dianisidine (ODA) when complexed with a vanadium ion. Vanadium haloperoxidases of the invention can also be identified by the presence of a catalytic frame helical motif (sometimes referred to herein as a "catalytic bundle") exemplified by residues 435 to residue 631 in SEQ ID NO:2. The catalytic frame motif of a haloperoxidase comprises the helices immediately part of or adjacent to the three conserved vanadium-binding regions identified below. The fourth helix of the catalytic frame can be either upstream of the equivalent of α1 in the *Fucus* sequence (as in the fungal haloperoxidases wherein the four helical frame is composed of helices K, L, N, and O and L, N and O are associated with vanadate binding site) or equivalent to α4 in the *Fucus* sequence. Polypeptides of the invention typically have a sequence at least about 70% identical (as determined below), usually at least about 80% identical to the sequence from residue 435 to residue 631 in SEQ ID NO:2. One of skill will recognize that the sequence of the polypeptide can be altered without substantially altering activity of the polypeptide (e.g., by conservative substitutions). In addition, as explained below, less conservative modifications (e.g., substitutions, additions, and deletions) can be made to facilitate proper refolding, purification, and the like, as desired.

Full length vanadium haloperoxidase polypeptides of the invention typically have a mass of about 73.4 kDa, and have a sequence as shown in SEQ ID NO:2. One of skill will recognize that shorter vanadium haloperoxidase polypeptides can also be used. For instance, the polypeptides can consist essentially of the C terminal region described above. The polypeptides may thus comprise from about 90 amino acids to about 300 amino acids, or from about 120 to about 250 amino acids. Exemplary polypeptide having a mass of about 20 kDa or less are described in detail below.

A "polynucleotide sequence encoding a vanadium haloperoxidase polypeptide" of the invention is a polynucleotide which encodes a vanadium peroxidase polypeptide as described above. Thus, the nucleic acids of the invention can be altered by substitutions, deletions, and additions, as desired. Polynucleotide sequences of the invention will typically be at least about 60%, usually at least about 70%, more usually at least about 80%, and often at least about 90% or 95% identical to a subsequence of SEQ ID NO:1 which encodes 435 to residue 631 in SEQ ID NO:2. Polynucleotides of the invention can also be identified by their ability to hybridize under defined conditions to such a nucleic acid. Means for determining this are described in detail below.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual organism or cell is a polynucleotide which is introduced into the organism or cell using genetic engineering techniques.

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

A "promoter" is defined as an array of nucleic acid control sequences that direct transcription of an operably linked nucleic acid. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

In the case where the inserted polynucleotide sequence is transcribed and translated to produce a functional polypeptide, one of skill will recognize that because of codon degeneracy a number of polynucleotide sequences will encode the same polypeptide. In addition, the term specifically includes those sequences substantially identical (determined as described below) with polynucleotide sequences disclosed here.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably at least about 70% or 80%, most preferably 90 or 95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of an algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altshul, et al., *J. Mol. Biol.*, 215:403–410 (1990)). These initial neighborhood word hits act as seeds for initiating searches to find longer HSPs containing them. The word hits are extended in both directions along each sequence for as far as the cumulative aligmnent score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. One of skill will recognize, however, that conservative amino acid substitutions may still affect the properties of the protein in terms of polarity, hydrophobicity, enzymatic activity, and the like. Similarly, less conservative amino acid substitutions may have little effect on the properties of the protein, depending, for example, on the region of the protein in which the substitution is made.

The following six groups each contain amino acids that are conservative substitutions for one another:
1) Alanine (A), Serine (S), Threonine (T);
2) Aspartic acid (D), Glutaric acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

(see, e.g., Creighton, *Proteins* (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

In the present invention, genomic DNA or cDNA comprising nucleic acids useful in the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

BRIEF DESCRIPTION OF THE DRAWINGS

FIG. 3 shows the results of experiments testing the enzymatic activity of truncated enzymes of the invention.

FIG. 4 shows the differences in the F4R5 regions of the *Fucus* and *Ascophyllum* haloperoxidase sequences.

FIG. 5 shows motifs conserved among algal and fungal haloperoxidases (SEQ ID NOS:9, 12 and 13, 10, 14–16 and 11, and 17–19, respectively).

DETAILED DESCRIPTION OF THE INVENTION

Figure 1:
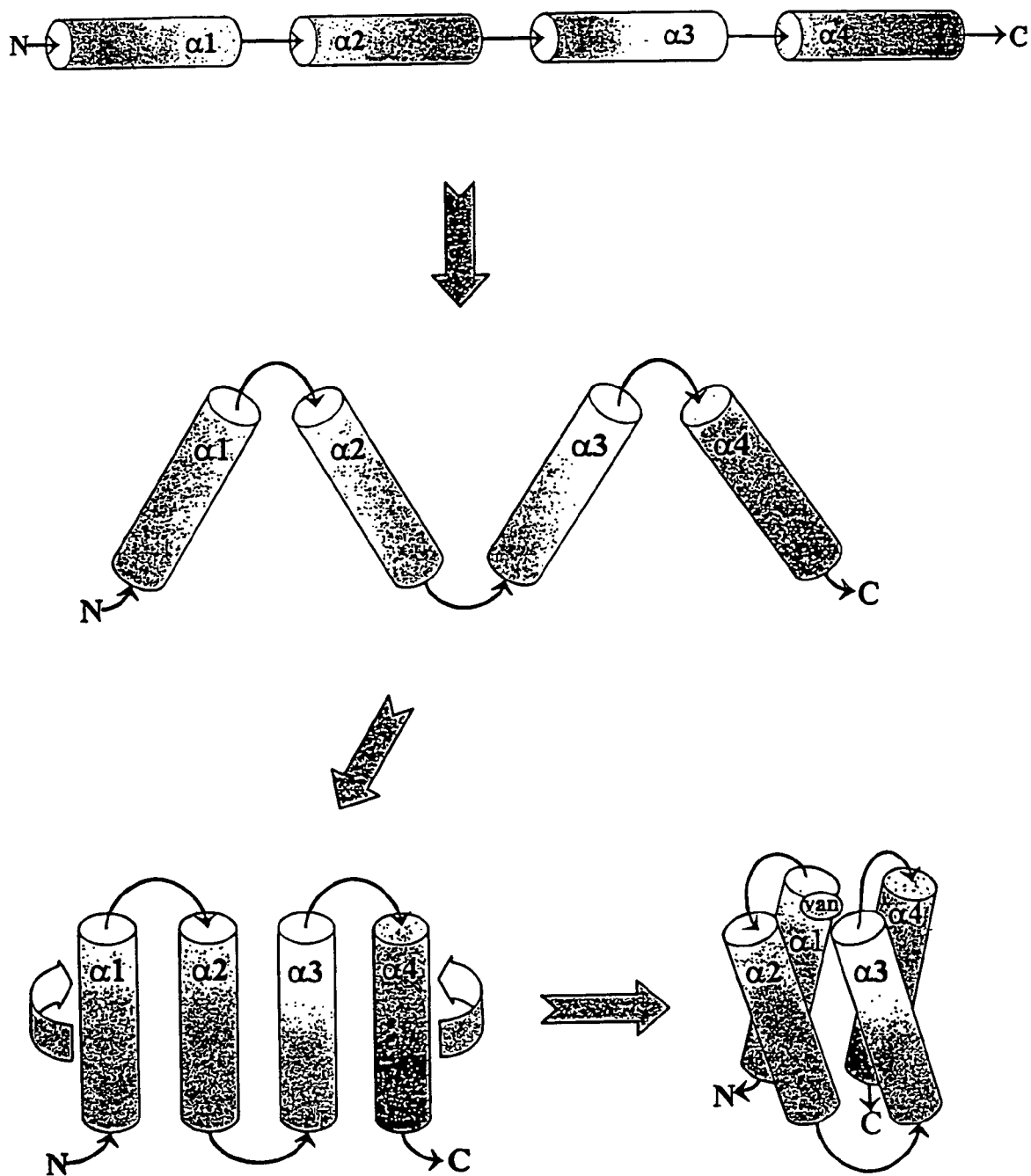
FIG. 1 shows the catalytic frame of the *Fucus* vanadium peroxidase.

The practice of this invention involves the construction of recombinant nucleic acids and the expression of genes in transfected host cells. Molecular cloning techniques to achieve these ends are known in the art. A wide variety of cloning and in vitro amplification methods suitable for the construction of recombinant nucleic acids such as expression vectors are well-known to persons of skill. Examples of these techniques and instructions sufficient to direct persons of skill through many cloning exercises are found in Sambrook et al., *Molecular Cloning: A Laboratory Manual, 2nd Ed.,* Vols. 1–3, Cold Spring Harbor Laboratory (1989); Berger and Kimmel, *Guide to Molecular Cloning Techniques, Methods in Enzymology* volume 152 Academic Press, Inc., San Diego, Calif.; and *Current Protocols in Molecular Biology,* F. M. Ausubel et al., eds., Current Protocols, a joint venture between Greene Publishing Associates, Inc. and John Wiley & Sons, Inc. (1994 Supplement).

Preparation of Nucleic Acids of the Invention

Nucleic acids encoding vanadium bromoperoxidase polypeptides of this invention can be prepared by any suitable method known in the art, including, for example, cloning and restriction of appropriate sequences or direct chemical synthesis by methods such as the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.*, 22: 1859–1862; and the solid support method of U.S. Pat. No. 4,458,066.

In one preferred embodiment, the desired nucleic acids encoding a vanadium bromoperoxidase are isolated by routine cloning methods. A nucleotide sequence encoding the enzyme (as provided below, for example) is used to construct probes that specifically hybridize to a bromoperoxidase gene in a genomic DNA sample, or to mRNA in a total RNA sample (e.g., in a Southern or Northern blot). Once the target nucleic acid is identified, it can be isolated according to standard methods known to those of skill in the art.

The desired nucleic acids can also be cloned using well known amplification techniques. Examples of protocols sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3: 81–94; (Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077–1080; Van Brunt (1990) *Biotechnology* 8: 291–294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039. Suitable primers for use in the amplification of the nucleic acids of the invention are described in the Example Section, below.

The desired nucleic acid can also be cloned by detecting its expressed product by means of assays based on the physical, chemical, or immunological properties of the expressed protein. For example, one can identify a cloned bromoperoxidase nucleic acid by the ability of a polypeptide encoded by the nucleic acid to catalyze the oxidation of o-dianisidine HCl (ODA) as described in the examples below.

In some embodiments, it may be desirable to modify the bromoperoxidase nucleic acids of the invention. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) *Gene* 8:81–97, Roberts et al. (1987) *Nature* 328: 731–734. The modified polypeptides can be tested for activity using the ODA assays described below.

Preparation of Expression Cassettes Encoding Bromoperoxidase Polypeptides of the Invention The nucleic acid sequences of the invention are incorporated into expression cassettes for high level expression in a desired host cell according to techniques well known to those of skill in the art. The particular host cell used is not critical to the invention and can be either a prokaryotic or eukaryotic cell, as described below.

A typical expression cassette contains a promoter operably linked to the desired DNA sequence. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21–25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

Either constitutive or regulated promoters can be used in the present invention. Regulated promoters can be advantageous because the host cells can be grown to high densities before expression of the bromoperoxidase polypeptides is induced. High level expression of heterologous proteins slows cell growth in some situations. Regulated promoters especially suitable for use in *E. coli* include the bacteriophage lambda $P_L$ promoter, the hybrid trp-lac promoter (Amann et al., *Gene* (1983) 25: 167; de Boer et al., *Proc. Natl. Acad. Sci. USA* (1983) 80: 21, and the bacteriophage T7 promoter (Studier et al., *J. Mol. Biol.* (1986); Tabor et al., (1985). These promoters and their use are discussed in Sambrook et al., supra.

For expression of the polypeptides in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in Bacillus in addition to *E. coli*.

A ribosome binding site (RBS) is conveniently included in the expression cassettes of the invention. An RBS in *E. coli*, for example, consists of a nucleotide sequence 3–9 nucleotides in length located 3–11 nucleotides upstream of the initiation codon (Shine and Dalgarno, *Nature* (1975) 254: 34; Steitz, *In Biological regulation and development: Gene expression* (ed. R. F. Goldberger), vol. 1, p. 349, 1979, Plenum Publishing, NY).

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297–16302.

The polypeptides can be expressed intracellularly, or can be secreted from the cell. Intracellular expression often results in high yields. If necessary, the amount of soluble, active polypeptide may be increased by performing refolding procedures (see, e.g., Sambrook et al., supra.; Marston et al., *Bio/Technology* (1984) 2: 800; Schoner et al., *Bio/Technology* (1985) 3: 151).

In embodiments in which the bromoperoxidase polypeptides are secreted from the cell, either into the periplasm or into the extracellular medium, the DNA sequence is linked to a cleavable signal peptide sequence. The signal sequence directs translocation of the bromoperoxidase polypeptide through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc. Natl. Acad. Sci. USA* 82: 7212 (1985); Talmadge et al., *Proc. Natl. Acad. Sci. USA*, 77:3988 (1980); Takahara et al., *J. Biol. Chem.*, 260:2670 (1985)).

One of skill would recognize that other modifications can be made to the bromoperoxidase polypeptides without diminishing their biological activity. Modifications may be made to improve various properties of the enzyme or to facilitate the cloning, expression, and the like. For example, the minimal catalytic frame helices disclosed here can be modified to have different surface properties and thereby increase frame stability. Such modifications are discussed in more detail below. Modifications to enhance cloning and expression are well known to those of skill in the art and include, for example, a methionine added at the amino terminus to provide an initiation site, or additional amino acids that form an purification tag (e.g., poly His) placed on either terminus to facilitate purification. In addition, one of skill will recognize that fusion proteins with various heterologous protein sequences can be prepared. For example, overexpression of a protein can lead to the accumulation of folding intermediates which have a tendency to aggregate. Production of fusion proteins including sequences, such as bacterial thioredoxin, can be used to facilitate proper folding. The polypeptides of the invention can also be fused to other proteins to allow quantification or localization of the linked protein. Thus, the fusion partner can be detected by the presence of the peroxidase activity of the enzyme of the invention. The fusion partner may also be a bacterial protein that results in increased yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook et al., supra.).

For certain applications, it may be desirable to cleave the non-bromoperoxidase amino acids from the fusion protein after purification. This can be accomplished by any of several methods known in the art, including cleavage by cyanogen bromide, a protease (e.g., enterokinase), or by Factor $X_a$, (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

A suitable system for obtaining recombinant proteins from *E. coli* which maintains the integrity of their N-termini has been described by Miller et al. *Biotechnology* 7:698–704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

Expression of Bromoperoxidase Polypeptides of the Invention

Bromoperoxidases of the invention can be expressed in a variety of host cells, including *E. coli*, other bacterial hosts, yeast, and various higher eukaryotic cells such as algal cells. For example microalgal expression systems, useful in the invention include the diatom *Phaeodactylum tricornutum* (Apt et al. *J. Phycol.* 32:4 (1996)).

Examples of useful bacteria include, but are not limited to, *Escherichia, Enterobacter, Azotobacter, Erwinia, Bacillus, Pseudomonas, Klebsielia, Proteus, Salmonella, Serratia, Shigella, Rhizobia, Vitreoscilla*, and *Paracoccus*. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The expression vectors of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant bromoperoxidase polypeptides can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology* Vol. 182: *Guide to Protein Purification.*, Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

When the proteins of the invention are expressed in bacteria, large amounts of the expressed protein is present in inclusion bodies. The wet weight of inclusion bodies produced is in the range of 1–4 mg/mL of bacterial culture, constituting up to 40% of total cell protein (Novagen). Following standard washing procedures, the inclusion bodies contain expressed protein up to 95% in purity. A preferred method of purifying the enzymes from inclusion bodies is to wash the protein from inclusion bodies and use a simple one step refolding procedure. One such method is to solublize the protein in alkali at pH 10–12 (e.g., with NaOH, KOH, Caps). The protein is then refolded in ammonium sulfate (preferably at pH 5.6 to 8.0)±minimolar levels of magnesium chloride at room temperature. Alternatively the protein can be refolded in magnesium sulfate up to about 0.5 M (pH 5.6–8.0) at between about 0° C. to about 10° C. The protein can also be refolded in imidazole and either sodium or potassium chloride, preferably at pH7–8 and preferably at 10–17° C., which is the temperature of the seawater in which the marine algae grow. Detergents such as Tween-20, BPer (Pierce Chemical Company) or BugBuster (Novagen) are optional in all three refolding procedures.

The purified haloperoxidase polypeptides of the invention can be used in a number of industrial applications. The polypeptides can be used for any purpose to which prior art haloperoxidases are used. For instance, the polypeptides can be used to halogenate various substrates, including proteins. For instance the polypeptides can be used to produce epoxides from alkenes, halogenated ketones from alkynes, to produce alpha, gamma-halohydrins from cyclopropanes, and to produce dihalogenated products from alkenes and alkynes. In addition, the ability of the polypeptides to oxidize various compounds make them useful, for instance, in signal generating systems in place of horseradish peroxidase. Thus, the haloperoxidase polypeptides of the invention can be used as a component in assays as described in WO 97/09619. The polypeptides can also be as enzymatic antimicrobial agents (see, e.g., WO 95/27046). Other uses include production of phenolic adhesives as described in U.S. Pat. No. 5,520,727.

Modified Haloperoxidase Polypeptides

Based on the results provided here, one of skill can readily construct and test a number modified haloperoxidases from brown algae, red algae (e.g., *Corallina*) and fungi (e.g., *Curvularia*). These modified enzymes can be designed using methods well known in the art for introducing modifications (e.g., substitutions, additions, and deletions) can be made to provide enhanced activity, stability, or to facilitate proper refolding, purification, and the like, as desired. These modified proteins can be tested for the desired properties using assays disclosed here.

As demonstrated below, the entire catalytic domain of the haloperoxidase enzymes is not necessary for catalytic activity (see, Example 2). The basic organization of haloperoxidase enzymes is a catalytic helical frame found at the core of the monomeric unit. In *Fucus* the helical frame is an M-shape or zig-zag with the vanadate-bound active site at the top of the "M" (see, FIG. 1). The helices forming the helical frame correspond to amino acids 439–631 of SEQ D NO: 1. The catalytic frame helices (CFH) 1-2-3-4 (see, Table 3) correspond to helices K-O-Q-R, respectively in the *Ascophyllum* enzyme X-ray structure as reported by Weyland et al. (1999). A protein fold to similar to the catalytic helical frame in the core of the brown algal enzymes is seen in the separate catalytic domain of the fungal enzymes (Barnett et al. *J Biol Chem* 273, 23381–7 (1998), although there is no homology between the *Ascophyllum* and fungal enzymes except at the conserved vanadate binding motifs. Differences in these folds include the length and helical content of the variable loop between the first and second vanadate binding sites, an elongated loop following the third vanadate binding site only for the fungal enzymes, and the presence of additional helices in the fungal catalytic domain. From site mutation studies on several vanadate binding amino acids in a fungal active site, Macedo-Ribeiro et al. *J Biol Inorg Chem* 4:209–19 (1999) concluded that the many hydrogen bonding and salt bridge interactions at the catalytic site of the fungal enzyme formed a very rigid matrix or frame for oxyanion binding.

Active truncated enzymes which consist of the catalytic frame helices of a particular enzyme can be prepared. In addition, the simple antiparallel helical motif can refold more easily when the loops which separate the frame helices are shortened. In the case of *Fucus*, the first two of the three helical intersections along the M-shaped bundle (between helices 1–2 and 2–3) can be minimized (see FIG. 2). These loops form gaps of 74 amino acids between helices 1 and 2 and 31 amino acids between helices 2 and 3 (in contrast to 4 amino acids between helices 3 and 4). As noted above, when the protein is expressed in bacterial cells, most of the expressed protein is in inclusion bodies. Shortening the loops greatly facilitates correct protein refolding from the inclusion bodies. Such modifications also change the protein surface properties, since the surface loops are both acidic. The isoelectric point changes from acidic (pI 5.5) to basic (pI 8.7–9.2) when both loops are minimized.

The removal of the helix 1–2 acidic surface loop covering the catalytic site situates the catalytic site on the surface of the recombinant enzyme, held in place by the rigid helical frame, instead of being buried deep in a narrow, funnel-shaped cavity as in the native enzyme. Greater access to the catalytic site has two important consequences: the enzymatic turnover rate increases and additional and larger substrates can be accommodated. The size of the minimal active helical frame will be in the 9–10 kDa range after maximal terminal and internal truncation.

Analysis of amino acid differences between the *Fucus* and *Ascophyllum* enzymes, especially in the catalytic bundle and conserved sites, can be used to design enzymes with improved properties. As shown in FIG. 4 and Table 1, of the twenty-one amino acid differences between the *Fucus* and *Ascophyllum* enzymes in the F4R5 region, three are near the first and second vanadium-binding amino acids and are likely to be involved in the several-fold greater activity of the *Fucus* enzyme. These three sites are Ala 455, Cys 457 and Val 525. As noted above, the *Fucus* enzyme is more active than the *Acophyllum* and other algal and fungal enzymes. Thus, haloperoxidase enzymes can be engineered to include one or more of the 21 unique amino acids from the *Fucus* sequence to improve the properties of a particular enzyme. To do this the corresponding amino acid residues in a second haloperoxidase (e.g., the *Ascophyllum* enzyme) are identified by comparison of the amino acid sequence as well as the secondary, tertiary and quaternary structure of the proteins (e.g., using X ray crystallography and other well known techniques) to identify those residues that correspond to the residues identified in Table 1. The three short conserved vanadate binding motifs, which can readily be recognized by sequence alignment, are shown in FIG. 5. They are always present in the same order, and include the algal bromoperoxidases, the fungal chloroperoxidases, and some groups of phosphatases (Hemrika et al., *Proc. Natl. Acad. Sci. U.S.A.* 94:2145–2149 (1997); Stukey and Carman *Protein Science* 6:469–72 (1997). The identified amino acid residues are then substituted with the corresponding *Fucus* residue. Alternatively, the catalytic helical frame can be modified to more closely approximate the geometry of the *Fucus* active site. The geometry at the vanadium haloperoxidase active site differed between *Ascophyllum* and *Curvularia* enzymes (see Weyland et al. 1999 and Wever et al. 1997), *Curvularia* single site mutants (see Macedo-Ribeiro et al. 1999) and among the three fungal enzymes (Barnett et al. 1998). The *Fucus* and *Ascophyllum* vanadium binding sites are very similar in primary sequence, except as noted in Table 1. The geometry of the catalytic site of the *Fucus* enzyme is clearly unique as demonstrated by its severalfold greater activity than other vanadium haloperoxidases. The modified enzymes can be readily tested for activity and other properties according to standard techniques.

TABLE 1

| Number | RVP × 1 Fucus Site | Location | Fucus/Asco. Amino acid Differences | Equivalent Ascophyllum Site |
|---|---|---|---|---|
| 1 | Thr439 | α1 helix | Polar/Hydrophobic | Ile320 |
| 2 | Ala455 | 1$^{st}$ van. Bind. | Hydrophobic/Polar | Ser336 |
| 3 | Cys457 | 1$^{st}$ van. Bind. | Small/Large | Trp338 |
| 4 | Asn478 | α1–α2 loop | Polar/Hydrophobic | Leu359 |
| 5 | Ala481 | α1–α2 loop | Hydrophobic/Basic | Lys362 |
| 6 | Asp483 | α1–α2 loop | Acidic/Acidic | Glu364 |
| 7 | Asp485 | α1–α2 loop | Acidic/Polar | Asn366 |
| 8 | Ile490 | α1–α2 loop | Both Hydrophobic | Leu371 |
| 9 | Asp496 | α1–α2 loop | Acidic/Hydrophobic | Ala377 |
| 10 | Glu504 | α1–α2 loop | Acid/Hydrophobic | Ala385 |
| 11 | Val525 | 2$^{nd}$ van. bind. | Hydrophobic/Acidic | Glu406 |
| 12 | Glu559 | α3–α4 loop | Both Acidic | Asp440 |
| 13 | Phe561 | α3–α4 loop | Hydrophobic Polar | Tyr442 |
| 14 | Asn563 | α3–α4 loop | Polar/Acidic | Asp444 |
| 15 | Phe566 | α3–α4 loop | Hydrophobic/Polar | Tyr447 |
| 16 | Ser568 | α3–α4 loop | Hydrophobic/Acidic | Asp449 |
| 17 | Glu573 | α3–α4 loop | Acidic/Basic | Lys454 |
| 18 | Asn576 | α3–α4 loop | Polar/Acidic | Asp457 |
| 19 | Glu578 | α3–α4 loop | Acidic/Basic | Arg459 |
| 20 | Ala580 | α3–α4 loop | Hydrophobic/Polar | Ser461 |
| 21 | Tyr584 | α3 helix | Polar/Hydrophobic | Phe465 |

EXAMPLE 1

This example describes the cloning of a vanadium bromoperoxidase gene of the invention.

Materials and Methods

DNA library. A *Fucus distichus* 2-cell embryos c-DNA library was prepared the λ-ZipLoxL1 plasmid (Gibco BRL, Gaithersburg, Md.) and is described in Goodner, et at., *Plant Physiology*, 107:1007–1008 (1995).

Antibody screening. An antibody to *Corallina vancouverensis* vanadium peroxidase was prepared which identified *Fucus distichus* vanadium peroxidase on Western blots of crude extracts.

DNA Hybridization Method. Hybridization probes were prepared at the second and near the third regions shown to be conserved between *Curvularia* and *Ascophyllum* vanadium peroxidase active sites by Messerschmidt, et al., *PNAS*, 93:392–396 (1996). Hybridization probes of 51 base pairs were designed with Oligo 5.0 Primer Analysis Software (National Biochemicals, Plymouth, Minn.), synthesized by Anagen (Palo Alto), and digoxigenin-labeled at the 5' end with the Genius system (BMB Biochemicals, Durham, N.C.). The sequence of the probe for the second conserved site was:

CCAACGCACCCTTCGTACCCGTCTGGC-
CACGCTACCCAAAACGGAGCATTT.

The sequence of the probe for the third conserved site was:
CCGTACGAACACTTCACCAGGAGCTGAT-
GACTTTCGCCGAGGAATCCACCT.

Sequencing. Sequencing of the *Fucus* vanadium peroxidase clone was accomplished by primer walking. M13 universal primers and primers designed from *Fucus* and *Ascophyllum* Vanadium haloperoxidase sequences with Oligo software and synthesized by Operon (Alameda, Calif.). ABI dye-terminator sequencing was done by the UCB Molecular and Cellular Biology DNA Sequencing Facility in Barker Hall.

Homology. DNA and protein searches on databases accessible online through GenBank using the BLAST algorithm (Altshul, et al., *J. Mol. Biol.*, 215:403–410 (1990)).

Protein Expression In order to optimize correct folding for peroxidase activity, recombinant *Fucus* vanadium peroxidase constructs were prepared and expressed in *E. coli* as fusion proteins with thioredoxin at the N-terminal end (pET-32 LIC Ligation Independent Cloning vector, Novagen, Madison, Wis.). This vector produces a high level of expression of soluble recombinant proteins in *E. coli* cytoplasm. While note necessary, the expressed protein can be fused with an N-terminal thioredoxin for optimizing correct protein folding, detection and purification, respectively (Novagen). In addition, an enterokinase (EK) cleavage site is located at the N-terminal end of the inserted protein so that native protein can be cleaved from the 19 kDa tagged peptide following expression. Three sizes of constructs were prepared for confirmation of the active site domain at the 3' end, as suggested by the minimal fungal-*Ascophyllum* homology reported at the active site (Messerschmidt, et al., *PNAS*, 93:392–396 (1996)). Expression constructs were prepared for the full length *Fucus* bromoperoxidase and two 5'-truncated forms (Table 2), corresponding to 100%, 80% and 54% of the full length sequence, respectively. The cloned λ-ZipLox plasmid containing the *Fucus* vanadium bromoperoxidase cDNA was used as the template for PCR amplification with Vent DNA polymerase (New England Biolabs, Beverly, Mass.).

TABLE 2

| Construct Designation | Starting point (bp #) on SEQ ID NO: 1 | VPx bp expressed | kDa of Vpx sequence | Expressed fusion protein size in kDa |
|---|---|---|---|---|
| rVP × 1 | 1 | 2028 | 73.5 | 93 |
| rVP × 2 | 409 | 1620 | 57.7 | 77 |
| rVP × 3 | 937 | 1092 | 39.6 | 59 |

The following Fucus peroxidase LIC primers were designed with Oligo software (National Biosciences, Inc., Plymouth, Minn.) and pET-32 LIC sequences necessary for incorporation into the vector. Primers for the 5' end were: GACGACGACAAGATGCTTTGCCATGCAGCGGACA (SEQ ID NO:5) (34 bp) for the full length construct, GACGACGACAAGATGGCGCCGAATA-GAAGGGACAA (SEQ ID NO:6) (35 bp) for the mid length construct, and GACGACGACAAGATGCTCTTCCGAGC-GACCTTC (SEQ ID NO:7) (33 bp) for the short construct. One 3'-primer, GAGGAGAAGCCCGGTTGCACTAAGC-CTGGCAGT (SEQ ID NO:8) (33 bp) was used for all three constructs. PCR was carried out for 30 cycles of 3 mm at 940, 1.5 mm at 55° C. and 2.3 mm at 72° C., in 7 mM MgSO4 for the full length construct and 4 mM MgSO4 for the two truncated constructs. The PCR products were electrophoresed in 1.5% agarose and stained with ethidium bromide. DNA was extracted from the excised bands in GenElute minus EtBr spincolumns (Supelco, Bellefonte, Pa.) and precipitated with ethanol.

Ligation independent cloning was carried out according to the pET-32 LIC protocol (Novagen), with a T4 DNA ligase (GibcoBRL, Grand Island, N.Y.) step added prior to transformation for the full length construct. The recombinant plasmids were transformed into the NovaBlue strain of $E.$ $coli$ according to the Novagen protocol. In all bacterial strains transformed, plasmid clones containing peroxidase inserts were identified by PCR of partial Fucus peroxidase sequences with Taq polymerase (Promega, Madison, Wis.) in 1.6–3.75 mM MgCl2 for 30 cycles of 3 min at 94°, 1.5 min at 45° and 2 min at 72°, followed by agarose electrophoresis. Plasmids cloned from NovaBlue cells were expressed in BL21(DE3), BL21(DE3) pLysS and AD494 (DE3) $E.$ $coli$ cells (Novagen). The AD494strain is deficient in thioredoxin reductase, which results in an appropriate redox potential for correct folding of eukaryotic proteins (Novagen). Induced bacterial cytoplasmic protein preparations were examined by protein electrophoresis, and the products were tested for vanadium-dependent peroxidase activity. Proteins were expressed for 0, 0.5, 1.5 and 3 h after induction of protein synthesis with IPTG (isopropylthio-b-galactoside). Bacterial lysates were prepared immediately after protein expression.

The recombinant bromoperoxidase proteins were immediately purified from bacterial cytoplasmic proteins by affinity chromatography. The HisTag (a sequence of 6 histidines, 6×His) in the fusion protein was bound to a nickel nitrilo-acetic acid (Ni+2-NTA) agarose column (Sigma, St. Louis, Mo.) according to the standard Qiagen protocol. The bound recombinant protein containing 6×His was eluted with 1M imidizole in 20 mM Tris-HCl pH 7.9 and 500 mM NaCl. Denatured protein samples were electrophoresed in 8% polyacrylamide gels containing 4% SDS, fixed and stained with Coomassie Brilliant Blue R250. The recombinant vanadium peroxidases (rVPx) were tested for vanadium-dependent peroxidase activity on dot blots. A preliminary in vitro expression experiment was carried out for the three LIC constructs in a bacteriophage transcription system linked with a rabbit reticulocyte translation system (Single Tube Protein System 2, T7, Novagen), and the products were tested for vanadium-dependent peroxidase activity on dot blots.

Vanadium peroxidase activity assay. Peroxidase activity with ODA (o-dianisidine HCl, Sigma) as the substrate was detected by dot blotting 1 µL of enzyme solution onto positively charged nylon membranes (Biodyne B, Pall Corp., Port Washington, N.Y.). Substrate solution contained 100 mM Tris-HCl, pH 8.0, 10 mM KBr, 0.25 mM urea-H2O2, and 1 mM ODA (Sigma). Quantitites of dry KBr, urea-$H_2O_2$ and ODA were estimated for daily substrate solutions.

RVPx were rapidly revanadated with trace levels of vanadium. 1 µL of 100 mM sodium orthovanadate in a 2 µL pipettor tip was ejected from the tip. The "vanadated" empty tip was then inserted into a 5–10 µL drop of enzyme solution on a piece of Parafilm (Fisher, Hayward, Calif.) and pipetted in and out 5 times. After waiting 1–5 min, 1 µL of the revanadated rVPx was pipetted onto the nylon membrane and air dried for a few minutes. While strong peroxidase activity was visible in a few minutes, the membrane was incubated in the ODA solution overnight.

Antibody labeling on Membranes (Plaque Lifts, Dot Blots and Western Blots). The membranes were blocked overnight at 4° C. in 100 mM Tris-HCl pH 8.0+4% skim milk+0.1% tween-20 and then incubated for 3 h at 37° C. in mouse ascites antibody to $Corallina$ vanadium peroxidase or mouse ascites control antibody (Sigma) diluted 1:1,000 in blocking solution. The blots were washed 3× in blocking solution and incubated in alkaline phosphatase-conjugated anti-mouse second antibody (diluted 1:5,000) for 1 h at room temperature. They were then washed 3× in blocking solution and rinsed in alkaline buffer (100 mM NaCl+100 mM Tris-HCl at pH 9.5.+50 mM MgCl2). Chemiluminescence was detected by of CPD-Star (BMB, Durham, N.C.) (diluted 1: in alkaline buffer) and exposed to X-ray film (Kodak) for 2 h. Alternative colorigenic detection was by overnight incubation in NBT/BCIP substrate (Pierce, Rockford, Ill.).

Results

Fucus cDNA library Screening. The fusion protein for the VPx clone which was expressed during cDNA screening was apparently truncated prior to the VPx start codon, at a TGA stop codon located at bases 82–84 in the 5' UTR. This truncation upstream of the VPx coding sequence caused a lack of VPx protein expression during screening, explaining the lack of a-VPx antibody labeling during extensive screening. Therefore, two 51 bp DNA probes based on two small regions of homology at the active site between $Curvularia$ chloroperoxidase and $Ascophyllum$ bromoperoxidase (Messerschmidt, et al., $PNAS$, 93:392–396 (1996)) were used to screen the $Fucus$ embryo cDNA library. Only one clone was identified which was labeled with both of the VPx DNA probes after extensive screening. This clone was about 3 kb in size after Not I/Sal I excision from the plasmid.

Fucus vanadium peroxidase sequence. The sequence of the VPX from 2-cell Fucus gardneri embryos is shown in SEQ ID NO:1 (see, also Genbank Accession No. AF053411). The 2931 base pairs in the Fucus cDNA clone includes 227 bases in the 5' UTR, 2031 bases in the coding region and 673 bases in the 3' UTR. The 5' UTR is a partial sequence, and the 3' UTR is complete. Translation of the VPx coding sequence produces a 73,353 Da protein containing 676 amino acids. No obvious leader peptide sequence was detected although VPx is secreted (Vreeland, et al., *Molecular Biology of the Cell* 7 (Supplement), 304a (1996)).

A 73.4 kDa Fucus monomer would be the largest known VPx monomer, although the molecular mass of the native *Fucus* enzyme is unknown. The 73.4 kDa size is larger than the 60 kDa VPx monomer from a related brown alga, *Ascophyllum nodosum*, as well as larger than the 67.5 kDa fungal *Curvularia inaequalis* chloroperoxidase monomer (Simons, et al., *European Journal of Biochemistry*, 229: 566–574 (1995)). The *Fucus* VPx monomer comigrated with the monomer of the red alga *Corallina vancouverensis* on PAGE gels (Vreeland, et al., *Molecular Biology of the Cell* 7 (Supplement), 304a (1996)). The *C. officinalis* and *C. pilulifera* VPx monomers are approximately 64 kDa based on SDS PAGE data (Itoh, et al., *J. Biological Chemistry* 261:5194–5200 (1986); Sheffield, et al., *Phytochemistry*, 32:21–26 (1993); Rush, et al., *FEBS Letters*, 359:244–246 (1995)), and the *Fucus* VPx monomer might therefore be expected to be a similar size. However, the related *Fucus* and *Ascophyllum* brown algal VPx monomer sizes differ, and it is also possible that the *C. vancouverensis* monomer size may differ from the published *C. officinalis* and *C. pilulifera* monomer size.

Alternative explanations include utilization of the third start codon in the *Fucus* VPx sequence to produce a 64,471 Da protein of 596 amino acids. Utilization of the third start codon is supported by the lack of a TATA box upstream of the first two start codons, and the presence of a TATA box 79 bp upstream of the third in-frame ATG. Also possible are different protein shape and/or charge properties resulting in electrophoretic comigration of *Fucus* and *C. vancouverensis* monomers.

The *Fucus* and *C. vancouverensis* multimers also comigrated, implying that the *Fucus* multimer may be a dodecamer (Vreeland, et al., *Molecular Biology of the Cell* 7 (Supplement), 304a (1996)) although the *Ascophyllum* multimer is a dimer (Vilter 1995), since the *C. officinalis* and *C. pilulifera* multimers appear to be dodecamers (Sheffield, et al., *Phytochemistry*, 32:21–26 (1993); Rush, et al. *FEBS Letters*, 359:244–246 (1995); Itoh, et al., *J. Biological Chemistry* 261:5194–5200 (1986)). Although the C-terminal catalytic domain appears to be similar in *Fucus* and *Ascophyllum* VPx, their self-associating domains are likely to differ due to their different monomer sizes. The *Fucus* VPx may contain more than one self-associating domain if it contains the double hexameric ring arrangement as found for the *C. pilulifera* VPx by Itoh, et al., *J. Biological Chemistry* 261:5194–5200 (1986), and this may partially account for the larger size of the *Fucus* VPx in the N-terminal region.

The *Fucus* and *Ascophyllum* brown algal VPx were 87.2% identical for 709 base pairs of DNA and 85.8% identical for 232 amino acids for the published partial C-terminal VPx sequence of *Ascophyllum* (Vilter 1995) when calculated from the best match of the Fucus data with the published *Ascophyllum* peptide and translated sequences. The amino acid sequence of the revised and completed *Ascophyllum* enzyme (Weyland et al. 1999) is 89% identical to the *Fucus* enzyme, and the Fucus enzyme is 123 amino acids longer at the N-terminus and one amino acid longer at the C-terminus.

The *Fucus* sequence contains three conserved vanadium-binding regions (Messerschmidt et al.). The three conserved vanadium-binding regions are as follows: (1) amino acids 452–473 AQRASCYQKWQVHRFARPEALG; (2) amino acids 528–546 PTHPSYPSGHATQNGAFAT and (3) amino acids 591–609 NKLAVNVAFGRQMLGIHYRFD. In the three conserved vanadium-binding regions the *Fucus* and *Ascophyllum* amino acid sequences differ only at two locations in the first conserved region (alanine at *Fucus* 455 substituted for serine at *Ascophyllum* 19, and cysteine at *Fucus* 457 substituted for tryptophan at *Ascophyllum* 21). These two amino acid differences are therefore likely to be related to the greater specific activity of the *Fucus* enzyme, as are other amino acid sequence differences in the catalytic frame (amino acids *Fucus* 441–636). A major difference between the *Fucus, Ascophyllum* and *Corallina* algal bromoperoxidases and the fungal chloroperoxidases and various phosphatases is the additional basic amino acids in the first conserved domain of the bromoperoxidases, histidine at *Fucus* 464 and leucine at *Fucus* 472 for the brown algal enzymes, with threonine instead of leucine for the *Corallina* enzyme. These additional amino acids in the first conserved region are likely to be related to the greater activity of the bromoperoxidases with bromide, which is larger than the chloride ion.

Bacterial expression of Fucus vanadium peroxidase constructs. The three recombinant Fucus VPx proteins (rVPx, Table 1) were expressed as soluble cytoplasmic proteins in both BL21(DES) and AD494 strains of *E. coli* at the expected sizes of recombinant proteins. All of the recombinant proteins were seen as major bands against the background of bacterial proteins. This represents production of about 1–10 mg/100 mL of recombinant proteins, as estimated from the intensity of Coomassie blue-stained bands.

After Ni-NTA column purification, peroxidase activity for rVPx expressed by AD494 cells was tested on dot blots with 0-dianisidine as substrate. No peroxidase activity was detected in the absence of added vanadium, although *E. coli* contains an 80 kDa o-dianisidine-reactive peroxidase. This result with an extremely sensitive activity assay also demonstrates that the single affinity purification step removed significant contamination by bacterial proteins.

Peroxidase activity was detected in all three rVPx constructs immediately following protein expression and purification, but only in the presence of added vanadium. The activity was relatively weak, and decreased with smaller rVPx construct size. However, after overnight treatment at −20° C., activity was much stronger and of similar intensity for all three construct sizes. Like native algal VPx, the recombinant forms bound to positively charged nylon membranes but did not bind to nitrocellulose membranes. However, the recombinant forms did not bind as tightly to nylon membranes.

The three sizes of rVPx were also expressed in an in vitro rabbit reticulocyte system. It was clear that expression of all three sizes of rVPx occurred, although background peroxidase activity was seen in this eukaryotic system.

Discussion

ODA is a common substrate for heme peroxidases such as horseradish peroxidase and other peroxidases. The product of ODA oxidation by algal vanadium peroxidase was not halogenated, although it is not known whether ODA oxidation by rVPx involves a halogenated intermediate or singlet O2 production. The expression of active rVPx in *E. coli* demonstrates that glycosylation is not necessary for enzyme activity, and, indeed, the native enzyme is probably not glycosylated. Activity of recombinant enzyme shows that it can be folded correctly in bacterial cytoplasm, as well.

EXAMPLE 2

This example describes identification of the minimal catalytic unit of the enzymes of the invention.

As noted above, the X-ray structure of fungal and algal vanadium peroxidases have been reported Messerschmidt and Wever, (1996), Weyand et al., (1999) and Littlechild, (1999), supra. The algal catalytic helical bundle is found at the core of the monomeric unit, and a more loosely-organized region is found on the side of the core bundle near the catalytic site and away from the dimerization site. According to the *Ascophyllum* X-ray structure, this outer region consists of helices D, E, F, and H (from the N-terminal half of the protein) which are associated with helices L, M and N (forming a surface loop derived from the middle of the catalytic core bundle of the C-terminal catalytic unit).

Figure 2:
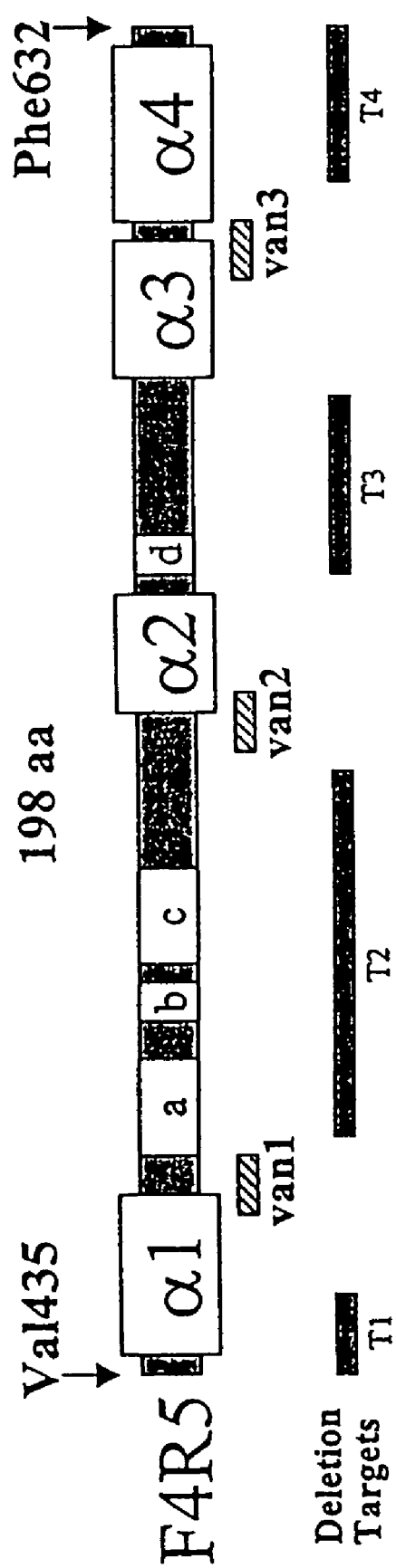
FIG. 2 shows the organization of the α-helices in the F4R5 active fragment of the invention. Catalytic frame helices are labeled α1–α4, and non-frame helices in intervening loops are indicated as a–d. The location of vanadium-binding amino acid motifs are shown at van1–van3. Deletions at both terminal (T1, T4) and internal (T2, T3) truncation targets further reduce the active vanadium peroxidase in size and promote rapid refolding of solubilized inclusion bodies.

The basic organization of the helical frame of the *Fucus* enzyme is an M-shape or zig-zag with the vanadate-bound active site at the top of the "M" (see, FIG. 1). The helices forming the helical frame and correspond to amino acids 439–631 of SEQ ID NO: 1. FIG. 2 and Table 3 show the catalytic frame helices (CFH) and helices included in the intervening loops. These helices were identified by comparison with *Curvularia* and *Ascophyllum* haloperoxidase X-ray structures and with the PepTools protein prediction program (Bio Tools, Inc.). CFH 1–2–3–4 correspond to helices K-O-Q-R, respectively, for the *Ascophyllum* enzyme X-ray structure as reported by Weyland et al. (1999).

TABLE 3

| CFH α-Helix | Amino Acid Location | Length in Amino Acids | Homologous Ascophyllum α-Helix |
|---|---|---|---|
| 1 | Thr439-Trp461 | 23 | K |
| a* | Pro469-Ala481 | 13 | L |
| b* | Ile490-Leu493 | 4 | M |
| c* | Asp496-Gln509 | 14 | N |
| 2 | Gly536-Ile552 | 17 | O |
| d** | Leu554-Gly557 | 4 | P |
| 3 | Try584-Leu602 | 19 | Q |
| 4 | Arg607-Thr631 | 25 | R |

*helices in the CFH α1–α2 loop
**helix in the CFH α2–α3 loop

Further analysis of the *Fucus* enzyme revealed that the entire catalytic domain is not necessary for catalytic activity. A number of truncated enzymes were prepared and tested using the assays described in Example 1. The results are presented in FIG. 3. These experiments revealed that the only part needed for vanadium-dependent catalytic activity is the actual catalytic helical bundle. Active enzyme fragments consisting of only the 198 amino acids of the sequence between the 1–4 helices were found (e.g., fragment F4R5 in FIG. 2). Further N- and C-terminal truncation can also be made. In particular, the exposed ends of the 1 and 4 helices are involved in dimerization, and can be shortened, for an additional size reduction to 19.2 kDa while retaining catalytic activity.

The above examples are provided to illustrate the invention but not to limit its scope. Other variants of the invention will be readily apparent to one of ordinary skill in the art and are encompassed by the appended claims. All publications, GenBank Accession references (sequences), patents and patent applications cited herein are hereby expressly incorporated by reference for all purposes.

---

What is claimed is:

1. An isolated polypeptide comprising a vanadium haloperoxidase polypeptide consisting of a catalytic domain that complexes a vanadium ion and catalyzes the oxidation of o-dianisidine (ODA), wherein the vanadium haloperoxidase polypeptide comprises an amino acid sequence having at least 90% sequence identity to the sequence from residue 435 to residue 632 of SEQ ID NO:2, and has a molecular weight of no more than 40 kDa.

2. The isolated polypeptide of claim 1, wherein the polypeptide comprises an Ala residue at a position corresponding to position 455 of SEQ ID NO: 2, a Cys residue at a position corresponding to position 457 of SEQ ID NO: 2, and a Val residue at position 525 of SEQ ID NO: 2.

3. The isolated polypeptide of claim 1, wherein the polypeptide has at least 95% identity to a polypeptide as set forth in SEQ ID NO:2.

4. The isolated polypeptide of claim 1, wherein the amino acid sequence is residue 435 to residue 632 of SEQ ID NO:2.

5. The isolated polypeptide of claim 1, wherein the polypeptide has a molecular weight of about 20 kDa.

6. The isolated polypeptide of claim 1, wherein the polypeptide is immobilized on a solid surface.

7. The isolated polypeptide of claim 1, wherein the polypeptide further comprises a cleavable linker sequence.

8. The isolated polypeptide of claim 7, wherein the cleavable linker sequence is an enterokinase cleavable linker sequence.

9. The isolated polypeptide of claim 1, wherein the polypeptide further comprises an purification tag.

10. The isolated polypeptide of claim 9, wherein the purification tag comprises a plurality of histidine residues.

* * * * *

SEQUENCE LISTING

<160> NUMBER OF SEQ ID NOS: 20

<210> SEQ ID NO 1
<211> LENGTH: 2931
<212> TYPE: DNA
<213> ORGANISM: Fucus distichus
<220> FEATURE:
<221> NAME/KEY: CDS
<222> LOCATION: (228)..(2258)
<223> OTHER INFORMATION: vanadium bromoperoxidase

<400> SEQUENCE: 1

```
cgcggacaag ccttggaaga gaggttgccc aattcaacag agcgaggccc gtgaaggtgt      60
ggaggacacg tgctacaagc tgatccacga gagcctcaac ttccctactg atacgggagt     120
ttgtactgcg ccgcgttgcc aaaaaccgca actttaaaca gcgctcgcga gcgccacatg     180
cttcccacgc atccacaaaa tcgacagtgg tatcgctgag cttgaat atg ctt tgc       236
                                                    Met Leu Cys
                                                      1 cat gca gcg gac acg aca aga ggc tct cct atg cct gac acc gga gtg       284
His Ala Ala Asp Thr Thr Arg Gly Ser Pro Met Pro Asp Thr Gly Val
      5                  10                  15 ctt cgg ttg ctc aca tca gag cag cgc gct aaa ggt tgg aga cgc cag       332
Leu Arg Leu Leu Thr Ser Glu Gln Arg Ala Lys Gly Trp Arg Arg Gln
```

```
             20                  25                  30                  35
tta gag ggg gag aaa tca cta ggt ttt cat cca agc gag acg cct tat          380
Leu Glu Gly Glu Lys Ser Leu Gly Phe His Pro Ser Glu Thr Pro Tyr
                    40                  45                  50 atc aag tac ttg gaa ggc tct gag act tgg aag aag gtt aag ctt cca          428
Ile Lys Tyr Leu Glu Gly Ser Glu Thr Trp Lys Lys Val Lys Leu Pro
            55                  60                  65 acg gac ggc ata tcg gct tcc aag atc ctg ggt aaa att atg gcc agg          476
Thr Asp Gly Ile Ser Ala Ser Lys Ile Leu Gly Lys Ile Met Ala Arg
        70                  75                  80 gtc cgc atc gct acc gcc ttg gct gtg gta ctg gcc gca ccc tgt ttg          524
Val Arg Ile Ala Thr Ala Leu Ala Val Val Leu Ala Ala Pro Cys Leu
    85                  90                  95 gca ttc gac gag gtc aca gcc agt ggt gtt ttc cct gag gaa cac aag          572
Ala Phe Asp Glu Val Thr Ala Ser Gly Val Phe Pro Glu Glu His Lys
100                 105                 110                 115 cac acc ggg gag gga aga cac ctc cag acc tgt aca aac tcc gac gat          620
His Thr Gly Glu Gly Arg His Leu Gln Thr Cys Thr Asn Ser Asp Asp
                    120                 125                 130 gcg ctg gat ccg acg gcg ccg aat aga agg gac aac gta gct ttt gcg          668
Ala Leu Asp Pro Thr Ala Pro Asn Arg Arg Asp Asn Val Ala Phe Ala
            135                 140                 145 tcg cgg cgc gat gcc gcc agg cga gaa cgt gac ggg aca ggg act gtc          716
Ser Arg Arg Asp Ala Ala Arg Arg Glu Arg Asp Gly Thr Gly Thr Val
        150                 155                 160 tgc caa atc act aac gga gaa act gat ttg gct acc atg ttc cac aag          764
Cys Gln Ile Thr Asn Gly Glu Thr Asp Leu Ala Thr Met Phe His Lys
    165                 170                 175 tct ctg cca cac gat gaa ctg gga cag gta acc gca gac gac ttc gct          812
Ser Leu Pro His Asp Glu Leu Gly Gln Val Thr Ala Asp Asp Phe Ala
180                 185                 190                 195 atc ctc gag gac tgc atc tta aac gga gat ttc agc att tgc gag gac          860
Ile Leu Glu Asp Cys Ile Leu Asn Gly Asp Phe Ser Ile Cys Glu Asp
                    200                 205                 210 gtg cct gcg gga gac ccg gcg ggt cgc ctc gtc aat cct acc gct gcg          908
Val Pro Ala Gly Asp Pro Ala Gly Arg Leu Val Asn Pro Thr Ala Ala
            215                 220                 225 ttt gcc atc gac ata tcc ggt ccc gca ttc tcg gct acg aca ata ccc          956
Phe Ala Ile Asp Ile Ser Gly Pro Ala Phe Ser Ala Thr Thr Ile Pro
        230                 235                 240 ccg gta cct acc ctt tcc tct cct gag ctc gcc gct cag ttg gcg gag         1004
Pro Val Pro Thr Leu Ser Ser Pro Glu Leu Ala Ala Gln Leu Ala Glu
    245                 250                 255 cta tac tgg atg gcg ctg gcc agg gat gta ccc ttt atg cag tat ggc         1052
Leu Tyr Trp Met Ala Leu Ala Arg Asp Val Pro Phe Met Gln Tyr Gly
260                 265                 270                 275 acc gac gaa att acc act acc gcg gca gcc aac ctc gct gga atg gga         1100
Thr Asp Glu Ile Thr Thr Thr Ala Ala Ala Asn Leu Ala Gly Met Gly
                    280                 285                 290 ggc ttc cca aat ctg gac gcc gtg tcg ata ggg tcc gat ggt acg gtg         1148
Gly Phe Pro Asn Leu Asp Ala Val Ser Ile Gly Ser Asp Gly Thr Val
            295                 300                 305 gac ccg ttc tcc cag ctc ttc cga gcg acc ttc gtt ggt gtt gaa acg         1196
Asp Pro Phe Ser Gln Leu Phe Arg Ala Thr Phe Val Gly Val Glu Thr
        310                 315                 320 ggg ccc ttt gtc tct cag ctg ctc gtg aac agc ttc acc atc gac gct         1244
Gly Pro Phe Val Ser Gln Leu Leu Val Asn Ser Phe Thr Ile Asp Ala
    325                 330                 335 att acg gtc gaa ccg aag cag gag aca ttc gcc ccc gac ttg aac tat         1292
```

```
                Ile Thr Val Glu Pro Lys Gln Glu Thr Phe Ala Pro Asp Leu Asn Tyr
                340                 345                 350                 355 atg gtc gat ttt gac gaa tgg ctg aac att cag aat ggt gga ccc ccg               1340
Met Val Asp Phe Asp Glu Trp Leu Asn Ile Gln Asn Gly Gly Pro Pro
                360                 365                 370 gcc ggc ccc gaa gag tta gac gaa gag ctg cgt ttt atc cgt aac gcc               1388
Ala Gly Pro Glu Glu Leu Asp Glu Glu Leu Arg Phe Ile Arg Asn Ala
            375                 380                 385 cgc gac ctg gcc agg gtc tcc ttc gtg gac aat atc aac acc gaa gct               1436
Arg Asp Leu Ala Arg Val Ser Phe Val Asp Asn Ile Asn Thr Glu Ala
        390                 395                 400 tat cgc ggg tct ctt atc cta ctt gag ctg gga gcc ttc agc agg ccc               1484
Tyr Arg Gly Ser Leu Ile Leu Leu Glu Leu Gly Ala Phe Ser Arg Pro
    405                 410                 415 ggt atc aac ggt cca ttc atc gac agt gat cgg cag gcg ggc ttc gtc               1532
Gly Ile Asn Gly Pro Phe Ile Asp Ser Asp Arg Gln Ala Gly Phe Val
420                 425                 430                 435 aac ttc ggc acg tct cac tac ttc aga ttg ata ggt gcc gcc gag ctg               1580
Asn Phe Gly Thr Ser His Tyr Phe Arg Leu Ile Gly Ala Ala Glu Leu
                440                 445                 450 gcg cag cgt gcc tcg tgt tac caa aag tgg cag gtg cat cga ttt gca               1628
Ala Gln Arg Ala Ser Cys Tyr Gln Lys Trp Gln Val His Arg Phe Ala
            455                 460                 465 cgc ccc gag gct ctc ggg ggt acc ctc cac aac acc atc gcg ggg gat               1676
Arg Pro Glu Ala Leu Gly Gly Thr Leu His Asn Thr Ile Ala Gly Asp
        470                 475                 480 cta gat gca gac ttc gac atc tcc ctt ctt gaa aat gat gag ctc ttg               1724
Leu Asp Ala Asp Phe Asp Ile Ser Leu Leu Glu Asn Asp Glu Leu Leu
    485                 490                 495 aaa cgt gtg gcg gag ata aat gcg gcg cag aat ccc aac aac gag gtc               1772
Lys Arg Val Ala Glu Ile Asn Ala Ala Gln Asn Pro Asn Asn Glu Val
500                 505                 510                 515 acc tac ctt ctt cca caa gct atc caa gtg gga tcg cca acg cac cct               1820
Thr Tyr Leu Leu Pro Gln Ala Ile Gln Val Gly Ser Pro Thr His Pro
                520                 525                 530 tcc tac ccg tcc ggc cac gct acc caa aat gga gca ttt gcc aca gtt               1868
Ser Tyr Pro Ser Gly His Ala Thr Gln Asn Gly Ala Phe Ala Thr Val
            535                 540                 545 ctg aag gcc ctc att ggc cta gat cgg gga ggt gag tgc ttc cct aac               1916
Leu Lys Ala Leu Ile Gly Leu Asp Arg Gly Gly Glu Cys Phe Pro Asn
        550                 555                 560 ccc gtg ttc cca agc gat gac ggc ctg gaa cta atc aac ttc gaa ggg               1964
Pro Val Phe Pro Ser Asp Asp Gly Leu Glu Leu Ile Asn Phe Glu Gly
    565                 570                 575 gca tgc tta aca tat gag gga gag atc aac aag ctc gcg gtc aac gtc               2012
Ala Cys Leu Thr Tyr Glu Gly Glu Ile Asn Lys Leu Ala Val Asn Val
580                 585                 590                 595 gca ttt ggg agg cag atg ctg ggc atc cac tat cgg ttc gac ggt atc               2060
Ala Phe Gly Arg Gln Met Leu Gly Ile His Tyr Arg Phe Asp Gly Ile
                600                 605                 610 caa ggc cta ctt ctc gga gag aca atc act gta cga aca ctt cac cag               2108
Gln Gly Leu Leu Leu Gly Glu Thr Ile Thr Val Arg Thr Leu His Gln
            615                 620                 625 gag ctg atg acg ttc gcc gag gaa gcc acc ttt gaa ttc cgc tta ttc               2156
Glu Leu Met Thr Phe Ala Glu Glu Ala Thr Phe Glu Phe Arg Leu Phe
        630                 635                 640 acc gga gag gtc atc aaa ctt ttc cag gac ggg aca ttc tcc atc gat               2204
Thr Gly Glu Val Ile Lys Leu Phe Gln Asp Gly Thr Phe Ser Ile Asp
    645                 650                 655
```

```
gga gat atg tgt tcc ggt ttg gtt tac act ggc gtg gcg gac tgc cag    2252
Gly Asp Met Cys Ser Gly Leu Val Tyr Thr Gly Val Ala Asp Cys Gln
660             665                 670                 675 gct                                                                 2305
Ala      tagtgcagaa aataataatt gtcggatgct aaaatgcac ccacgaccaa gtcgtcgagt cacgtcgccg gagcatcctt cagcgaaaaa ggagagtaac ctatatgcta   2365
tagaggagaa ccacggagta caatgcaggt tcttttacca tgtacattgg attgcagtaa   2425
gtgcggttag agagggatac gttaaacgtg cttgcctgtg tatatgatac atttgtcatg   2485
gaaatattag aatgcgttga cttgacttca ccatgaaata ccatgatcgc gtggtgtgct   2545
gctttcacct gtcggagcgg tacgtaagat gtgctttcta ctgagccgtt tgtgtttagt   2605
ccattccgcg tggcagtgta aacaaagagg atgtagtctc gccctcagtt tggagagtac   2665
cgtaggtggc aggacgtata tctctggtag cggtctgtta agaacttcca caagaccgtt   2725
tacgtttggt tgtttagtcg atgcctcttc gttacttgac cgatccattg agagtacctg   2785
taccagtatg gtgtaagaca tatttttctc ctgttatgga tctgtagaac agctaggtgt   2845
tgttttatac acaggatgct ataaaatagg gatgttgata atggcatcgg tactcatgaa   2905
accgcaaaat ggcgatagat attccc                                       2931

<210> SEQ ID NO 2
<211> LENGTH: 676
<212> TYPE: PRT
<213> ORGANISM: Fucus distichus

<400> SEQUENCE: 2

Met Leu Cys His Ala Ala Asp Thr Thr Arg Gly Ser Pro Met Pro Asp
  1               5                  10                  15

Thr Gly Val Leu Arg Leu Leu Thr Ser Glu Gln Arg Ala Lys Gly Trp
             20                  25                  30

Arg Arg Gln Leu Glu Gly Glu Lys Ser Leu Gly Phe His Pro Ser Glu
         35                  40                  45

Thr Pro Tyr Ile Lys Tyr Leu Glu Gly Ser Glu Thr Trp Lys Lys Val
     50                  55                  60

Lys Leu Pro Thr Asp Gly Ile Ser Ala Ser Lys Ile Leu Gly Lys Ile
 65                  70                  75                  80

Met Ala Arg Val Arg Ile Ala Thr Ala Leu Ala Val Val Leu Ala Ala
                 85                  90                  95

Pro Cys Leu Ala Phe Asp Glu Val Thr Ala Ser Gly Val Phe Pro Glu
            100                 105                 110

Glu His Lys His Thr Gly Glu Gly Arg His Leu Gln Thr Cys Thr Asn
        115                 120                 125

Ser Asp Asp Ala Leu Asp Pro Thr Ala Pro Asn Arg Arg Asp Asn Val
    130                 135                 140

Ala Phe Ala Ser Arg Arg Asp Ala Ala Arg Arg Glu Arg Asp Gly Thr
145                 150                 155                 160

Gly Thr Val Cys Gln Ile Thr Asn Gly Glu Thr Asp Leu Ala Thr Met
                165                 170                 175

Phe His Lys Ser Leu Pro His Asp Glu Leu Gly Gln Val Thr Ala Asp
            180                 185                 190

Asp Phe Ala Ile Leu Glu Asp Cys Ile Leu Asn Gly Asp Phe Ser Ile
        195                 200                 205

Cys Glu Asp Val Pro Ala Gly Asp Pro Ala Gly Arg Leu Val Asn Pro
    210                 215                 220
```

```
Thr Ala Ala Phe Ala Ile Asp Ile Ser Gly Pro Ala Phe Ser Ala Thr
225                 230                 235                 240

Thr Ile Pro Pro Val Pro Thr Leu Ser Ser Pro Glu Leu Ala Ala Gln
            245                 250                 255

Leu Ala Glu Leu Tyr Trp Met Ala Leu Ala Arg Asp Val Pro Phe Met
            260                 265                 270

Gln Tyr Gly Thr Asp Glu Ile Thr Thr Thr Ala Ala Ala Asn Leu Ala
        275                 280                 285

Gly Met Gly Gly Phe Pro Asn Leu Asp Ala Val Ser Ile Gly Ser Asp
        290                 295                 300

Gly Thr Val Asp Pro Phe Ser Gln Leu Phe Arg Ala Thr Phe Val Gly
305                 310                 315                 320

Val Glu Thr Gly Pro Phe Val Ser Gln Leu Leu Val Asn Ser Phe Thr
                325                 330                 335

Ile Asp Ala Ile Thr Val Glu Pro Lys Gln Glu Thr Phe Ala Pro Asp
                340                 345                 350

Leu Asn Tyr Met Val Asp Phe Asp Glu Trp Leu Asn Ile Gln Asn Gly
            355                 360                 365

Gly Pro Pro Ala Gly Pro Glu Glu Leu Asp Glu Leu Arg Phe Ile
370                 375                 380

Arg Asn Ala Arg Asp Leu Ala Arg Val Ser Phe Val Asp Asn Ile Asn
385                 390                 395                 400

Thr Glu Ala Tyr Arg Gly Ser Leu Ile Leu Leu Glu Leu Gly Ala Phe
                405                 410                 415

Ser Arg Pro Gly Ile Asn Gly Pro Phe Ile Asp Ser Asp Arg Gln Ala
                420                 425                 430

Gly Phe Val Asn Phe Gly Thr Ser His Tyr Phe Arg Leu Ile Gly Ala
            435                 440                 445

Ala Glu Leu Ala Gln Arg Ala Ser Cys Tyr Gln Lys Trp Gln Val His
450                 455                 460

Arg Phe Ala Arg Pro Glu Ala Leu Gly Gly Thr Leu His Asn Thr Ile
465                 470                 475                 480

Ala Gly Asp Leu Asp Ala Asp Phe Asp Ile Ser Leu Leu Glu Asn Asp
                485                 490                 495

Glu Leu Leu Lys Arg Val Ala Glu Ile Asn Ala Ala Gln Asn Pro Asn
            500                 505                 510

Asn Glu Val Thr Tyr Leu Leu Pro Gln Ala Ile Gln Val Gly Ser Pro
        515                 520                 525

Thr His Pro Ser Tyr Pro Ser Gly His Ala Thr Gln Asn Gly Ala Phe
        530                 535                 540

Ala Thr Val Leu Lys Ala Leu Ile Gly Leu Asp Arg Gly Gly Glu Cys
545                 550                 555                 560

Phe Pro Asn Pro Val Phe Pro Ser Asp Asp Gly Leu Glu Leu Ile Asn
                565                 570                 575

Phe Glu Gly Ala Cys Leu Thr Tyr Glu Gly Glu Ile Asn Lys Leu Ala
            580                 585                 590

Val Asn Val Ala Phe Gly Arg Gln Met Leu Gly Ile His Tyr Arg Phe
        595                 600                 605

Asp Gly Ile Gln Gly Leu Leu Leu Gly Glu Thr Ile Thr Val Arg Thr
        610                 615                 620

Leu His Gln Glu Leu Met Thr Phe Ala Glu Glu Ala Thr Phe Glu Phe
625                 630                 635                 640

Arg Leu Phe Thr Gly Glu Val Ile Lys Leu Phe Gln Asp Gly Thr Phe
```

```
                     645                 650                 655
Ser Ile Asp Gly Asp Met Cys Ser Gly Leu Val Tyr Thr Gly Val Ala
            660                 665                 670

Asp Cys Gln Ala
        675

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence:probe for
      second conserved region between Curvularia and
      Ascophyllum vanadium peroxidase active sites

<400> SEQUENCE: 3
ccaacgcacc cttcgtaccc gtctggccac gctacccaaa acggagcatt t          51

<210> SEQ ID NO 4
<211> LENGTH: 51
<212> TYPE: DNA
<213> ORGANISM: Artificial Sequence
<220> FEATURE:
<223> OTHER INFORMATION: Description of Artificial Sequence:probe for
      third conserved region between Curvularia and
      Ascophyllum vanadium peroxidase active sites

<400> SEQUENCE: 4
ccgtacgaac acttcaccag gagctgatga ctttcgccga ggaatccacc t          51

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence:Fucus
      peroxidase ligation independent cloning (LIC) 5'
      primer for full length construct

<400> SEQUENCE: 5
gacgacgaca atatgctttg ccatgcagcg gaca                             34

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence:Fucus
      peroxidase ligation independent cloning (LIC) 5'
      primer for mid length construct

<400> SEQUENCE: 6
gacgacgaca agatggcgcc gaatagaagg gacaa                            35

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence:Fucus
      peroxidase ligation independent cloning (LIC) 5'
      primer for short construct

<400> SEQUENCE: 7
gacgacgaca agatgctctt ccgagcgacc ttc                              33
```

```
<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence:Fucus
      peroxidase ligation independent cloning (LIC) 3'
      primer for full length, mid length and short
      constructs

<400> SEQUENCE: 8
gaggagaagc ccggttgcac taagcctggc agt                                     33

<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence:conserved
      Fucus vanadium-binding region 1, amino acids 452-473,
      1st conserved motif

<400> SEQUENCE: 9

Ala Gln Arg Ala Ser Cys Tyr Gln Lys Trp Gln Val His Arg Phe Ala
  1               5                  10                  15

Arg Pro Glu Ala Leu Gly
            20

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence:conserved
      Fucus vanadium-binding region 2, amino acids 528-546,
      2nd conserved motif

<400> SEQUENCE: 10

Pro Thr His Pro Ser Tyr Pro Ser Gly His Ala Thr Gln Asn Gly Ala
  1               5                  10                  15

Phe Ala Thr

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence:conserved
      Fucus vanadium-binding region 3, amino acids 591-609,
      3rd conserved motif

<400> SEQUENCE: 11

Asn Lys Leu Ala Val Asn Val Ala Phe Gly Arg Gln Met Leu Gly Ile
  1               5                  10                  15

His Tyr Arg Phe Asp
            20

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence:1st
      conserved motif from algal haloperoxidases
<220> FEATURE:
<221> NAME/KEY: MOD_RES
<222> LOCATION: (1)..(22)
<223> OTHER INFORMATION: Xaa = any amino acid
```

<400> SEQUENCE: 12

Ala Xaa Xaa Xaa Xaa Xaa Tyr Gln Lys Xaa Xaa Xaa His Arg Xaa Xaa
 1               5                  10                  15

Arg Pro Glu Ala Xaa Gly
            20

<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence:1st
      conserved motif from algal and fungal haloperoxidases
<220> FEATURE:
<221> NAME/KEY: MOD_RES
<222> LOCATION: (2)..(11)
<223> OTHER INFORMATION: Xaa = any amino acid
<220> FEATURE:
<221> NAME/KEY: MOD_RES
<222> LOCATION: (12)
<223> OTHER INFORMATION: Xaa = any amino acid, present in algal enzymes
      only
<220> FEATURE:
<221> NAME/KEY: MOD_RES
<222> LOCATION: (13)..(19)
<223> OTHER INFORMATION: Xaa = any amino acid
<220> FEATURE:
<221> NAME/KEY: MOD_RES
<222> LOCATION: (20)
<223> OTHER INFORMATION: Xaa = any amino acid, present in algal enzymes
      only

<400> SEQUENCE: 13

Ala Xaa Xaa Xaa Xaa Xaa Xaa Xaa Lys Xaa Xaa Xaa Xaa Xaa Xaa Xaa
 1               5                  10                  15

Arg Pro Xaa Xaa Xaa Gly
            20

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence:2nd
      conserved motif from algal haloperoxidases
<220> FEATURE:
<221> NAME/KEY: MOD_RES
<222> LOCATION: (1)..(16)
<223> OTHER INFORMATION: Xaa = any amino acid

<400> SEQUENCE: 14

Pro Xaa His Pro Ser Tyr Xaa Ser Gly His Ala Xaa Xaa Xaa Gly Ala
 1               5                  10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence:2nd
      conserved motif from algal and fungal haloperoxidases
<220> FEATURE:
<221> NAME/KEY: MOD_RES
<222> LOCATION: (1)..(16)
<223> OTHER INFORMATION: Xaa = any amino acid

<400> SEQUENCE: 15

Pro Xaa Xaa Pro Xaa Tyr Xaa Ser Gly His Ala Xaa Xaa Xaa Gly Ala
 1               5                  10                  15

```
<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence:2nd
      conserved motif from algal and fungal haloperoxidases,
      phosphatases and other proteins
<220> FEATURE:
<221> NAME/KEY: MOD_RES
<222> LOCATION: (1)
<223> OTHER INFORMATION: Ser conserved in some proteins
<220> FEATURE:
<221> NAME/KEY: MOD_RES
<222> LOCATION: (2)
<223> OTHER INFORMATION: Tyr conserved in some proteins

<400> SEQUENCE: 16

Ser Tyr Pro Ser Gly His
 1               5

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence:3rd
      conserved motif from algal haloperoxidases
<220> FEATURE:
<221> NAME/KEY: MOD_RES
<222> LOCATION: (1)..(21)
<223> OTHER INFORMATION: Xaa = any amino acid

<400> SEQUENCE: 17

Asn Lys Leu Ala Xaa Asn Xaa Ala Xaa Gly Arg Xaa Met Xaa Gly Xaa
 1               5                  10                  15

His Tyr Xaa Xaa Asp
             20

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence:3rd
      conserved motif from algal and fungal haloperoxidases
<220> FEATURE:
<221> NAME/KEY: MOD_RES
<222> LOCATION: (1)..(14)
<223> OTHER INFORMATION: Xaa = any amino acid

<400> SEQUENCE: 18

Ala Xaa Xaa Arg Xaa Xaa Xaa Gly Xaa His Xaa Xaa Xaa Asp
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence:3rd
      conserved motif from algal and fungal haloperoxidases,
      phosphatases and other proteins
<220> FEATURE:
<221> NAME/KEY: MOD_RES
<222> LOCATION: (2)..(9)
<223> OTHER INFORMATION: Xaa = any amino acid
<220> FEATURE:
<221> NAME/KEY: MOD_RES
<222> LOCATION: (4)
```

```
-continued

<223> OTHER INFORMATION: Gly conserved in some proteins
<220> FEATURE:
<221> NAME/KEY: MOD_RES
<222> LOCATION: (10)
<223> OTHER INFORMATION: Asp conserved in some proteins

<400> SEQUENCE: 19

Arg Xaa Xaa Gly Xaa His Xaa Xaa Xaa Asp
 1               5                   10

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:6xHis
      purification tag

<400> SEQUENCE: 20

His His His His His His
 1               5
```